United States Patent
Cowley et al.

(10) Patent No.: US 9,737,212 B2
(45) Date of Patent: Aug. 22, 2017

(54) ELECTRONIC DEVICE SYSTEM TO DISPLAY BIOMETRIC FEEDBACK

(71) Applicant: Intel Corporation, Santa Clara, CA (US)

(72) Inventors: Nicholas Cowley, Wroughton (GB); Ruchir Saraswat, Swindon (GB); Richard Goldman, Cirencester (GB)

(73) Assignee: Intel Corporation, Santa Clara, CA (US)

( * ) Notice: Subject to any disclaimer, the term of this patent is extended or adjusted under 35 U.S.C. 154(b) by 93 days.

(21) Appl. No.: 14/583,220

(22) Filed: Dec. 26, 2014

(65) Prior Publication Data

US 2016/0183795 A1    Jun. 30, 2016

(51) Int. Cl.
*G08B 23/00* (2006.01)
*G08C 15/06* (2006.01)
*G08B 19/00* (2006.01)
*G08B 21/00* (2006.01)
*A61B 5/00* (2006.01)
(Continued)

(52) U.S. Cl.
CPC ........ *A61B 5/0015* (2013.01); *A61B 5/02438* (2013.01); *A61B 5/486* (2013.01); *A61B 5/681* (2013.01); *A61B 5/746* (2013.01); *G04G 17/083* (2013.01); *G04G 21/00* (2013.01); *G06F 19/3406* (2013.01); *G06F 19/3481* (2013.01); *G08B 21/182* (2013.01); *A61B 5/742* (2013.01)

(58) Field of Classification Search
CPC ... A61B 5/0002; A61B 5/681; A61B 5/02055; A61B 5/1112; A61B 5/0205; A61B 5/7275; A61B 5/742; A61B 5/02438; A61B 5/1118; A61B 5/6802; A61B 5/7445; A61B 5/746; A61B 2562/164; A61B 5/6824; A61B 5/6831
USPC ............. 340/870.02, 539.11–539.13, 870.09, 340/539.1
See application file for complete search history.

(56) References Cited

U.S. PATENT DOCUMENTS 6,619,835 B2 * 9/2003 Kita ..................... A44C 5/0015
368/10
6,736,759 B1 * 5/2004 Stubbs ................... A63B 22/00
482/5

(Continued)

FOREIGN PATENT DOCUMENTS

WO    WO 00-50963 A1    8/2000
WO    WO 2016/106027 A1    6/2016

OTHER PUBLICATIONS

International Search Report and Written Opinion in International Application No. PCT/US2015/065927, mailed on May 4, 2016, 14 pages.

(Continued)

*Primary Examiner* — Emily C Terrell
(74) *Attorney, Agent, or Firm* — Patent Capital Group

(57) ABSTRACT

Particular embodiments described herein provide for an electronic device, such as a wrist worn electronic device. One particular example implementation of the electronic device may include a main housing, a main display in the main housing, a wrist strap that allows the main housing to be secured to a user such that the main display is located on top of a wrist of the user, and a secondary display located on the wrist strap, where the secondary display communicates information to the user without the user having to turn the wrist.

25 Claims, 14 Drawing Sheets

(51) Int. Cl.
*G04G 21/00* (2010.01)
*G08B 21/18* (2006.01)
*G04G 17/08* (2006.01)
*A61B 5/024* (2006.01)
*G06F 19/00* (2011.01)

(56) References Cited

U.S. PATENT DOCUMENTS

| | | | | |
|---|---|---|---|---|
| 6,832,109 | B2* | 12/2004 | Nissila | A61B 5/0245 |
| | | | | 600/509 |
| 8,988,349 | B2* | 3/2015 | Alberth | G06F 1/163 |
| | | | | 345/158 |
| 9,288,836 | B1* | 3/2016 | Clement | H04W 84/18 |
| 2001/0008074 | A1 | 7/2001 | Radley-Smith | |
| 2004/0020856 | A1* | 2/2004 | Wong | A63B 24/00 |
| | | | | 210/656 |
| 2004/0152957 | A1* | 8/2004 | Stivoric | A61B 5/01 |
| | | | | 600/300 |
| 2007/0279852 | A1 | 12/2007 | Daniel et al. | |
| 2012/0293323 | A1 | 11/2012 | Kaib et al. | |
| 2013/0222271 | A1 | 8/2013 | Alberth et al. | |
| 2014/0207264 | A1* | 7/2014 | Quy | A61B 5/1112 |
| | | | | 700/91 |
| 2014/0275852 | A1 | 9/2014 | Hong et al. | |
| 2014/0378777 | A1 | 12/2014 | Conrad et al. | |
| 2015/0026647 | A1* | 1/2015 | Park | G06F 3/0488 |
| | | | | 715/863 |
| 2015/0371516 | A1* | 12/2015 | Petersen | G08B 21/02 |
| | | | | 340/539.12 |

OTHER PUBLICATIONS

Oct. 5, 2016 Examination Opinion Notification and Search Report in TW Application No. 104139151, with English translation, 20 pages.

* cited by examiner

ELECTRONIC DEVICE SYSTEM TO DISPLAY BIOMETRIC FEEDBACK

TECHNICAL FIELD

Embodiments described herein generally relate to the field of electronic devices and, more particularly, to an electronic device that can display biometric feedback.

BACKGROUND

Wearable computers (also known as body-borne computers or wearables) are miniature electronic devices that are worn by a user under, with, or on top of clothing. This class of wearable technology has been developed for general or special purpose information technologies and media development. Wearable computers are especially useful for applications that require more complex computational support than just hardware coded logics (e.g., a digital watch). Some current wearable computers are often worn on a wrist of the user with a display positioned on the top of the wrist. The display is used to communicate data to the user and often, the data is only available by turning the wrist and display towards the user.

BRIEF DESCRIPTION OF THE DRAWINGS

Embodiments are illustrated by way of example and not by way of limitation in the FIGURES of the accompanying drawings, in which like references indicate similar elements and in which.

The FIGURES of the drawings are not necessarily drawn to scale, as their dimensions can be varied considerably without departing from the scope of the present disclosure.

DETAILED DESCRIPTION OF EXAMPLE EMBODIMENTS

Overview

An electronic device is provided in one example embodiment and includes a plurality of electronic components (which can include any type of components, elements, circuitry, etc.). One particular example implementation of the electronic device may include a main housing, a wrist strap that allows the main housing to be secured to a user such that the main housing is located on the top of the wrist, and a secondary display located on the wrist strap, where the secondary display communicates information to the user without the user having to turn their wrist. The electronic device can further include at least one biosensor to collect biometric data from the user. The collected biometric data may be analyzed and the analyzed biometric data can be communicated to the user on the secondary display.

The electronic device can further include a plurality of secondary displays located on the wrist strap where each of the plurality of secondary displays communicates different information to the user. In one example, one of the plurality of secondary displays communicates a target to a user and a different secondary display communicates analyzed biometric data related to the target. In another example, the secondary display communicates a first alarm when a first threshold is satisfied and a second alarm when a second threshold is satisfied, where the first alarm is different than the second alarm Example Embodiments The following detailed description sets forth example embodiments of apparatuses, methods, and systems relating to detachable display configurations for an electronic device. Features such as structure(s), function(s), and/or characteristic(s), for example, are described with reference to one embodiment as a matter of convenience; various embodiments may be implemented with any suitable one or more of the described features.

Figure 1:
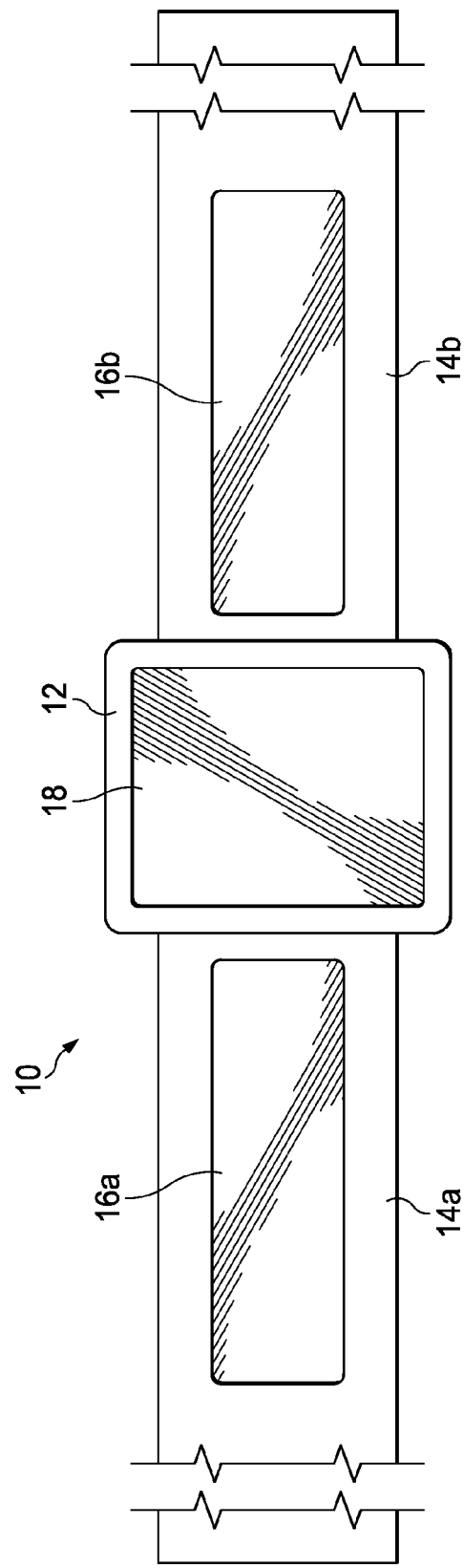
FIG. 1 is a simplified block diagram illustrating an embodiment of an electronic device in accordance with one embodiment of the present disclosure.

FIG. 1 is a simplified block diagram illustrating an embodiment of an electronic device 10 in accordance with one embodiment of the present disclosure. Electronic device 10 may include a main housing 12 and wrist straps 14a and 14b. Main housing 12 can include a main display 18. Wrist straps 14a and 14b can include secondary displays 16a and 16b respectively. Wrist straps 14a and 14b may be located on opposite sides of main housing 12 and allow electronic device 10 to be worn on the wrist of a user. In one or more embodiments, only one secondary display is included on one wrist strap. In other emboimdents, a plurality of secondary displays are included on one or more wrist straps.

Main display 18 can be a liquid crystal display (LCD) display screen, a light-emitting diode (LED) display screen, an organic light-emitting diode (OLED) display screen, a plasma display screen, or any other suitable display screen system. Main display 18 may be a touchscreen that can detect the presence and location of a touch on main display 18. Main housing 12 may include a battery and various electronics (e.g., processor, memory, etc.) to allow main housing 12 to operate as a standalone electronic device. In another embodiment, main housing 12 may include a wireless module (e.g., Wi-Fi module, Bluetooth module, etc.). In yet another embodiment, main housing 12 may include a camera, a microphone, and speakers. In one or more embodiments, secondary displays 16a and 16b can each be a liquid crystal display (LCD) display screen, a light-emitting diode (LED) display screen, an organic light-emitting diode (OLED) display screen, a plasma display screen, or any other suitable display screen system. Secondary displays 16a and 16b may each be a touchscreen that can detect the presence and location of a touch on secondary displays 16a and 16b.

In one or more embodiments, electronic device 10 is a wearable computer. In still other embodiments, electronic device 10 may be any suitable electronic device having a display such as a mobile device, a tablet device (e.g., i-Pad™, Phablet™, a personal digital assistant (PDA), a smartphone, an audio system, a movie player of any type, a computer docking station, etc. In yet another embodiment, most of the electronics (e.g., processor, memory, etc.) for electronic device 10 reside in main housing 12. If electronic device 10 is not worn on the wrist of a user, then secondary displays 16a and 16b may be positioned on electronic device at a location that allows information to be communicated to a user without having the user to adjust or move electronic device 10 when electronic device 10 is in use.

In general terms, electronic device 10 can be configured to be worn on the wrist of a user and to provide feedback or communications to the user in a readily assimilateable form. Electronic device 10 can include wrist straps (e.g., wrist straps 14a and 14b) and the angle of the wrist straps can be configured to provide a proper viewing angle of secondary displays (e.g., secondary displays 16a and 16b) located on the wrist straps. The feedback or communications may be in the form of a change in color in the one or more secondary displays, length of an illuminated bar on one or more secondary displays, an intensity or brightness of one or more secondary displays, etc. The feedback or communications may include two or more such indicators where the indicators may provide two or more types of feedback or communications. For example, a biometric sensor may monitor biometric data (e.g., pulse rate, step rate, respiration, etc) and one or more secondary displays may provide feedback or communications regarding the monitored biometric data. In an example, some of the indicators may be target data that is used to compare with the monitored biometric data.

For purposes of illustrating certain example features of electronic device 10, the following foundational information may be viewed as a basis from which the present disclosure may be properly explained. Current wrist worn wearable computers such as health monitoring/fitness aid devices are physically similar to a wristwatch. There are many form factors and materials for such devices but they all share a common feature set in that there is typically a display positioned on the top of the wrist of a user and a strap coupled to the display to hold the device around the wrist. Such an arrangement is not conducive to observing presented information or alerts, particularly when the user is involved in some form of physical activity, since the user has to interrupt the physical activity and adjust their position to enable them to observe the information or alert. Often, data is only available by turning the wrist and display towards the user and thus potentially interrupting exercise sessions.

In addition, a degree of interpretation is often require for current configurations of wrist worn computers as data is often displayed on alphanumeric displays and intensive exercise sessions can interfere with a user's ability to concentrate and interpret the displayed data. Further, the impact of any visible warning indicators are restricted by the current form factor of wrist worn computers since the user has to make a conscious decision to turn their wrist in order to view the display. What is needed is a new observability method that can provide a means for readily observing, for example, biofeedback data or other information or alerts.

Particular embodiments described herein provide for an electronic device, such as a wearable computer that includes a circuit board coupled to a plurality of electronic components (which includes any type of components, elements, circuitry, etc.). The electronic device may also include a wrist strap and biosensors to collect biometric data. The term "biometric data" is meant to include information that can be captured from a user's body such as heart rate, galvanic skin response (GSR), hydration, step count, step rate, body temperature, respiration, etc. The wrist strap can include one or more secondary displays and be configured to provide a visible feedback through the one or more secondary displays. In particular embodiments, the one or more secondary displays can be configured to display a moving or variable position visible light, change color, or otherwise provide a visual indication or alert to a user. Each of the one or more secondary displays may be independent of the other one or more secondary displays or may complement the other one or more secondary displays. In an embodiment, each of the one or more secondary displays can provide a visible representation of biofeedback or similar information enabling a user to simply monitor one or more feedback/sensor indicators.

The location of the one or more secondary displays on the wristband can facilitate observation of the biometric data without interrupting physical activity or without adjusting body position as with present systems. In addition, visual indicators on the one or more secondary displays may help communication information more readily than existing methods which typically present character based information.

In an embodiment, the biometric data can include visible warnings, for example corresponding to over exertion. For example, a first indicator may be pulse rate where a first color may correspond to 'slow down' and a second color to 'stop immediately'; the second indicator may correspond to hydration levels where a first color may correspond to 'consider rehydration' and the second to 'take hydration now'. More specifically, when a user over exerts themselves, indicated by an increased pulse rate, heart rate, sweat rate, or other data collected by the biometric sensors, then one or more secondary displays may start to glow an amber or red color, where amber indicates a warning that a limit is being approached and red indicates that the user is over exerting. Different warnings may use different colors. For example an increased pulse rate may be displayed as orange to red, hydration may be displayed as cyan to blue, etc. Acquired biofeedback data about the user can be stored and used to analyze the user's performance and plan future exercises.

In one implementation, a user may have preprogrammed an exercise routine which includes a correlated pulse rate profile (e.g., a cardio vascular exercise where the target exercise heart rate (pulse) is sixty to eighty percent of the maximum heart rate). The one or more secondary displays can then provide visible feedback to track the current pulse rate against the correlated pulse rate profile. For example, one or more secondary displays may glow green when the pulse rate is within the target value, red when the pulse rate is above the target value, and blue when the pulse rate is below the target value. The glow or illumination may be continuous in nature or may be pulsed. The rate of the pulse may also be used to supplement feedback to the user and the illumination or glow of one or more secondary displays may change from amber to red if over exertion occurs and the pulsing rate may increase to emphasis the warning.

In another example, one or more secondary displays may be used to provide a continuous monitor of a health indicator such as pulse rate or heart rate for patients who may have health issues. A user may wear the electronic device for a predefined duration where the electronic device could provide a continuous monitor of biofeedback data associated with a health issue. A user's health care provider could set warning limits on the electronic device which the electronic device could continuously compare against the measured value, for example heart rate, and issue a warning or alert during a period of abnormal activity or if the biometric data exceeds an defined threshold. In another example, a biosensor could monitor the insulin levels of a diabetic and issue a warning or alert during a period of abnormal activity or if the levels satisfy a defined threshold. The above examples are for illustration purposes only and other similar examples where a biosensor monitors biometric data related to a user and issues a warning or alert during a period of abnormal activity or if the biometric data satisfies a defined threshold are within the scope of this disclosure.

In an embodiment, there may be two or more limits set and if the electronic device determines that a first limit is exceeded, one or more secondary displays could glow a first color, which might indicate that the user should take corrective action such as to stop any current physical activity. If the electronic device determines that the second limit is exceeded, one or more secondary displays could glow a second color, which might indicate that the user should take a more radical course of action such as take a medication or seek medical help.

Figure 2A:
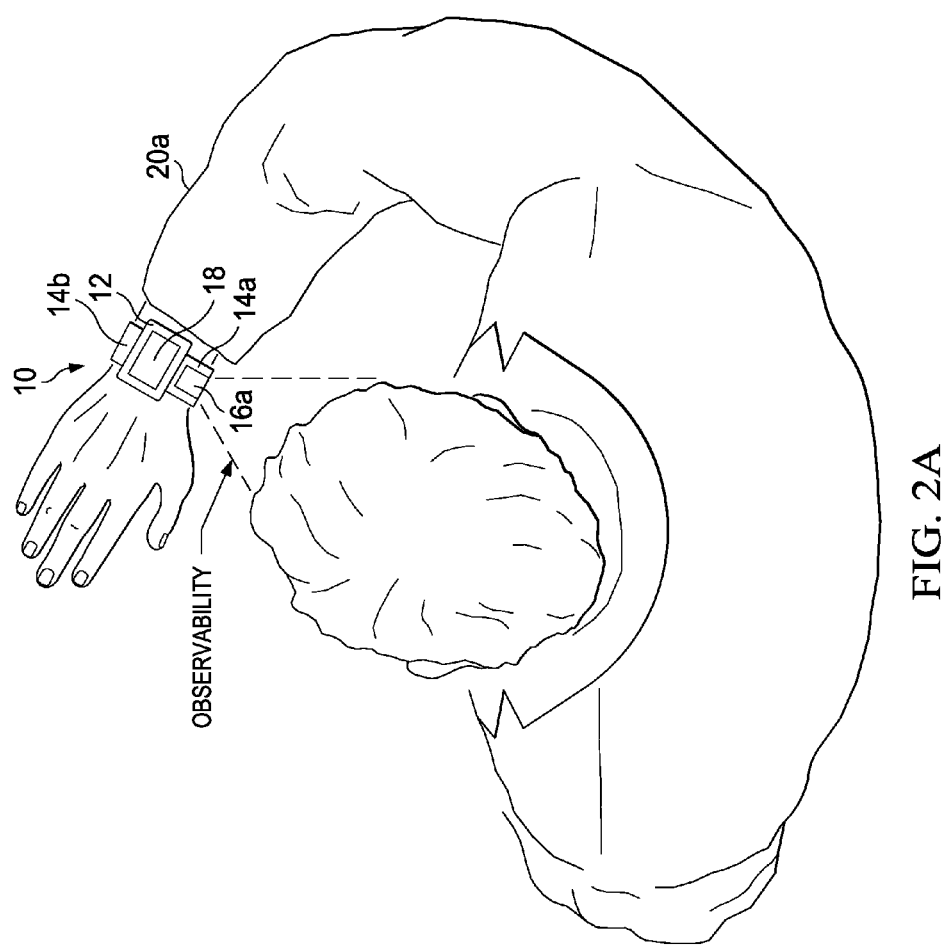
FIG. 2A is a simplified orthographic diagram illustrating an embodiment of an electronic device on a wrist of a user, in accordance with one embodiment of the present disclosure.
Figure 2B:
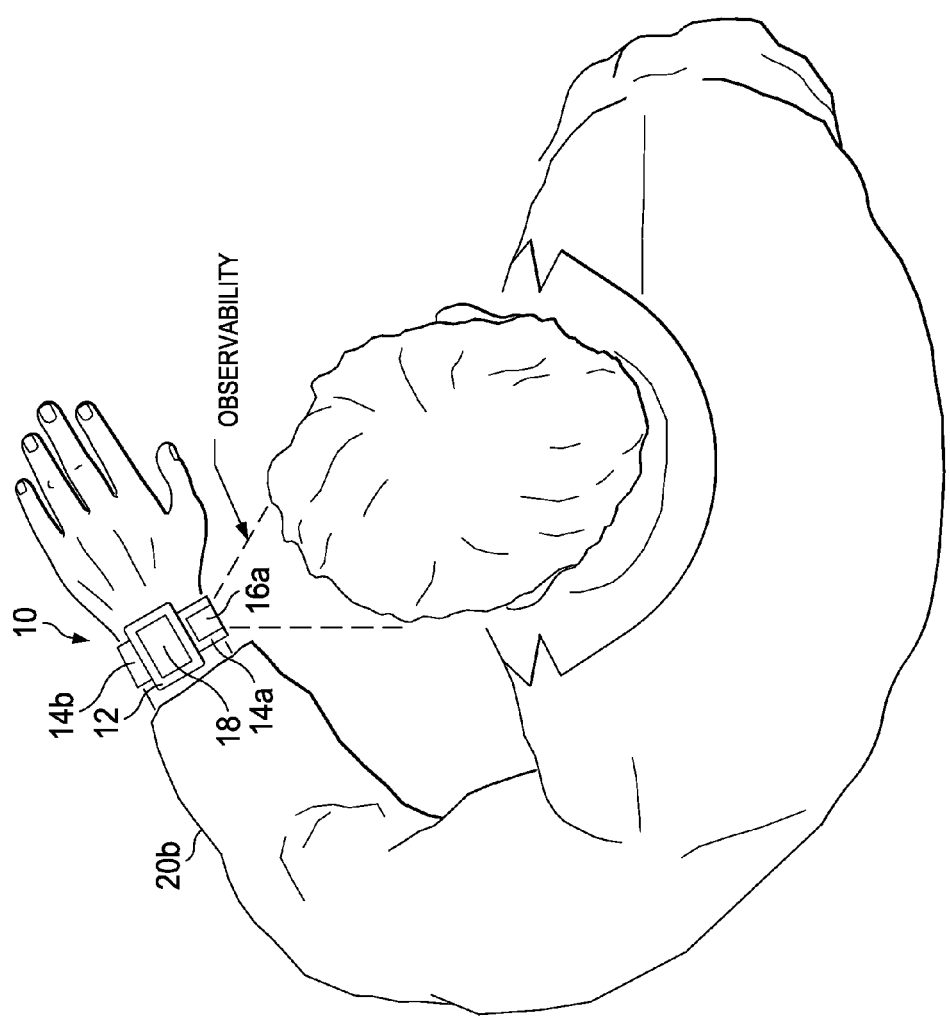
FIG. 2B is a simplified orthographic diagram illustrating an embodiment of an electronic device on a wrist of a user, in accordance with one embodiment of the present disclosure.

In another embodiment, the user can predefine an exercise routine that will require a certain pulse rate or respiration rate to be maintained where the desired pulse rate or respiration rate may vary during the exercise. To provide this feedback, one or more secondary displays may be configured to display three colors where, for example, a first color indicates the user is below the target rate, a second color indicates that the user is at the target rate, and a third color indicates that the user is above the target rate. The above examples are not intended to limit the number of indicators feedback by the illumination nor the number of warning levels associated with the indicator. The illumination may be pulsed and/or may cycle between two or more indicator feedback colors on one or more secondary displays Turning to FIG. 2A, FIG. 2A is a simplified schematic diagram illustrating an embodiment of electronic device 10, in accordance with one embodiment of the present disclosure. As illustrated in FIG. 2A, electronic device 10 can be worn on a right arm 20a of a user and secondary display 16a can be observed by the user without the user having to turn their wrist. Turning to FIG. 2B, FIG. 2B is a simplified schematic diagram illustrating an embodiment of electronic device 10, in accordance with one embodiment of the present disclosure. As illustrated in FIG. 2B, electronic device 10 can be worn on a left arm 20b of a user and secondary display 16a can be observed by the user without the user having to turn their wrist.

Figure 3A:
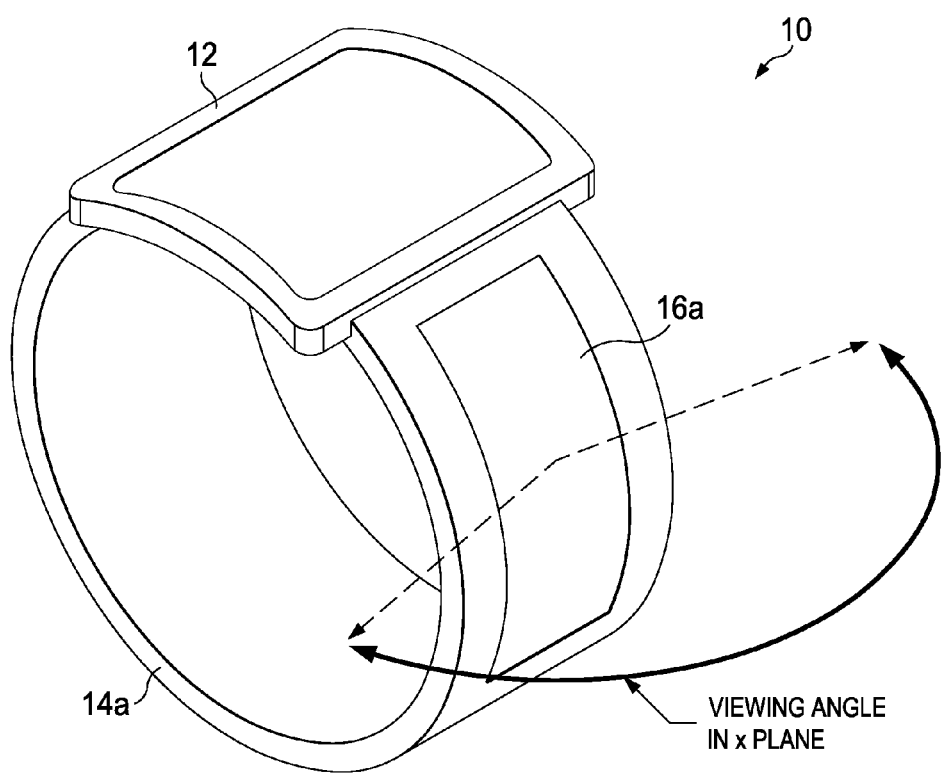
FIG. 3A is a simplified orthographic diagram illustrating an embodiment of an electronic device, in accordance with one embodiment of the present disclosure.
Figure 3B:
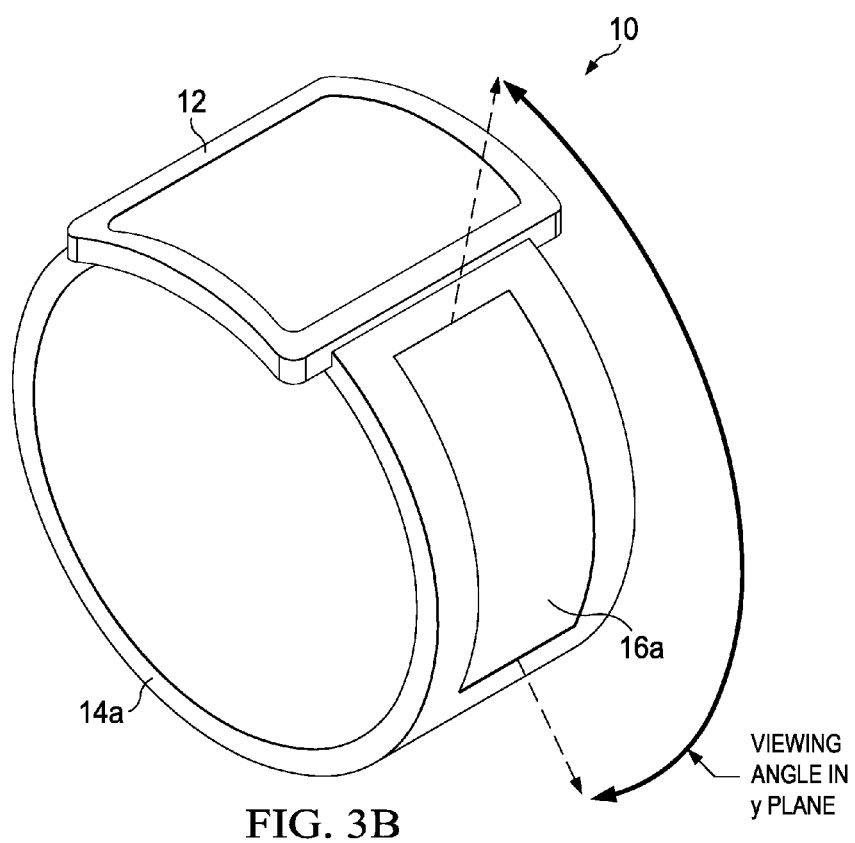
FIG. 3B is a simplified orthographic diagram illustrating an embodiment of an electronic device, in accordance with one embodiment of the present disclosure.

Turning to FIG. 3A, FIG. 3A is a simplified schematic diagram illustrating an embodiment of electronic device 10, in accordance with one embodiment of the present disclosure. As illustrated in FIG. 3A, the viewing angle of secondary display 16a in an X plane is relatively wide, thus allowing secondary display 16a to be observed by the user without the user having to turn their wrist. Turning to FIG. 3B, FIG. 3B is a simplified schematic diagram illustrating an embodiment of electronic device 10, in accordance with one embodiment of the present disclosure. As illustrated in FIG. 3B, the viewing angle of secondary display 16a in a Y plane is relatively wide, thus allowing secondary display 16a to be observed by the user without the user having to turn their wrist.

Figure 4:
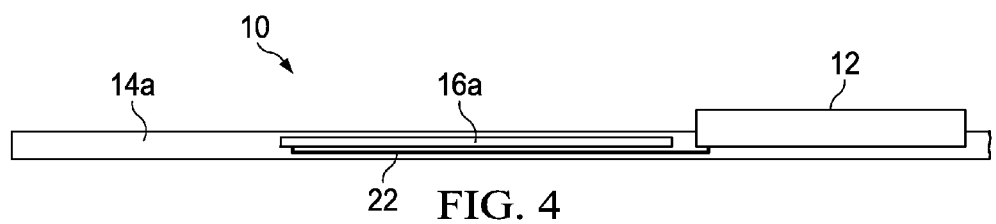
FIG. 4 is a simplified block diagram illustrating an embodiment of an electronic device, in accordance with one embodiment of the present disclosure.

Turning to FIG. 4, FIG. 4 is a simplified schematic diagram illustrating an embodiment of electronic device 10, in accordance with one embodiment of the present disclosure. In an embodiment, main housing 12 can be connected to secondary display 16a using an electrical connection 22. Electrical connection 22 can be configured to pass an electrical current and signals between main housing 12 and secondary display 16a (or any other secondary display) and provide a communication path between main housing 12 and secondary display 16a.

Figure 5:
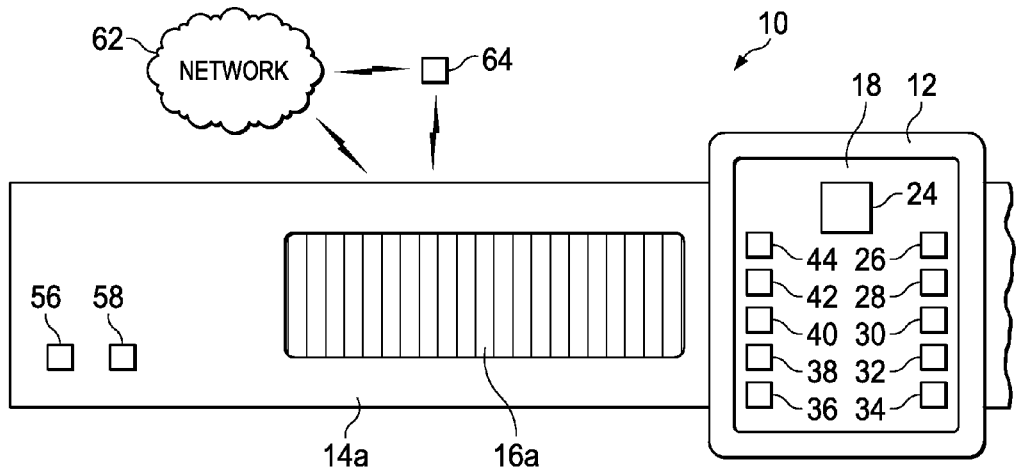
FIG. 5 is a simplified block diagram illustrating an embodiment of an electronic device, in accordance with one embodiment of the present disclosure.

Turning to FIG. 5, FIG. 5 is a simplified schematic diagram illustrating an embodiment of electronic device 10, in accordance with one embodiment of the present disclosure. As illustrated in FIG. 5, main housing 12 can include a location module 26, an accelerometer 28, a gyroscope 30, a vibrating alert 32, an interconnect 34, a wireless module 36, a processor 38, memory 40, a first biosensor 42, and a second biosensor 44. Wrist strap 14a can include a third biosensor 56 and a fourth biosensor 58. Any number of biosensors may be located on electronic device 10 and the location of each biosensor can be any location that allows the biosensor to collect the data related to the biosensor.

Location module 26 can be configured to determine the location of electronic device 10. Location module 26 can include a global positioning system (GPS) device or some other device to determine the location of electronic device 10. Accelerometer 28 can be configured to measure acceleration and may be configured to measure proper acceleration (physical acceleration) as opposed to coordinate acceleration (rate of change of velocity). Gyroscope 30 can be configured to measure the orientation of electronic device 10. Gyroscope 30 can include a microchip-packaged MEMS gyroscope, solid-state ring laser gyroscope, fiber optic gyroscope, quantum gyroscope, etc. Vibrating alert 32 can be configured to provide a vibrating alert, alert, indication, etc. to a user. Vibrating alert 32 can include a small electric motor connected to an eccentric or unbalanced weight.

Interconnect 34 can facilitate electrical current and signals being passed through a plug-in connector (e.g., whose male side protrusion connects to main housing 12 and whose female side connects to another electronic device or vice-verse). Note that any number of connectors (e.g., Universal Serial Bus (USB) connectors (e.g., in compliance with the USB 3.0 Specification released in November 2008), Thunderbolt™ connectors, a non-standard connection point such as a docking connector, etc.) can be provisioned in conjunction with electronic device 10. [Thunderbolt™ and the Thunderbolt logo are trademarks of Intel Corporation in the U.S. and/or other countries.]. Virtually any other electrical connection methods could be used and, thus, are clearly within the scope of the present disclosure.

Wireless module 36 can be configured to wirelessly communicate (e.g., Bluetooth®, infrared data, wireless uniform serial bus (USB), etc.) with a network 62 and a second electronic device 64. Second electronic device 64 may be a remote sensor, Bluetooth radio, cell phone, etc. The communication between electronic device 10 and second electronic device 64 may include a personal area network (PAN), a body area network, (BAN) or some other type of network. Network 62 offers a communicative interface between nodes, and may be configured as any local area network (LAN), virtual local area network (VLAN), wide area network (WAN), wireless local area network (WLAN), metropolitan area network (MAN), Intranet, Extranet, virtual private network (VPN), and any other appropriate architecture or system that facilitates communications in a network environment, or any suitable combination thereof, including wired and/or wireless communication.

Processor 38 can be configured to execute software or an algorithm to perform activities as discussed herein. Processor 38 can execute any type of instructions associated with data to achieve the operations detailed herein. In one example, processor 38 can transform an element or an article (e.g., data) from one state or thing to another state or thing. In another example, the activities outlined herein may be implemented with fixed logic or programmable logic (e.g., software/computer instructions executed by processor 38) and the elements identified herein could be some type of a programmable processor, programmable digital logic (e.g., a field programmable gate array (FPGA), an EPROM, an EEPROM) or an ASIC that includes digital logic, software, code, electronic instructions, or any suitable combination thereof. Any of the potential processing elements and modules described herein should be construed as being encompassed within the broad term 'processor.'

Memory 40 can include memory elements for storing information to be used in the operations outlined herein. Electronic device 10 may keep information in any suitable memory element (e.g., random access memory (RAM), read-only memory (ROM), erasable programmable ROM (EPROM), electrically erasable programmable ROM (EEPROM), application specific integrated circuit (ASIC), etc.), software, hardware, firmware, or in any other suitable component, device, element, or object where appropriate and based on particular needs. Any of the memory items discussed herein should be construed as being encompassed within the broad term 'memory element.' Moreover, the information being used, tracked, sent, or received can be provided in any database, register, queue, table, cache, control list, or other storage structure, all of which can be referenced at any suitable timeframe. Any such storage options may also be included within the broad term 'memory element' as used herein.

First biosensor 42, second biosensor 44, third biosensor 56, and fourth biosensor 58 can each be a sensor used for the collection of biometric data and the detection of a physical change of a user or an analyte (i.e., a substance or chemical constituent that is of interest in an analytical procedure) that combines a biological component with a physicochemical detection. First biosensor 42, second biosensor 44, third biosensor 56, and fourth biosensor 58 can include a bioreceptor that is designed to interact with the specific analyte of interest to produce an effect measurable by a transducer. The type of biomolecule measured by each biosensor can vary widely.

Figure 6:
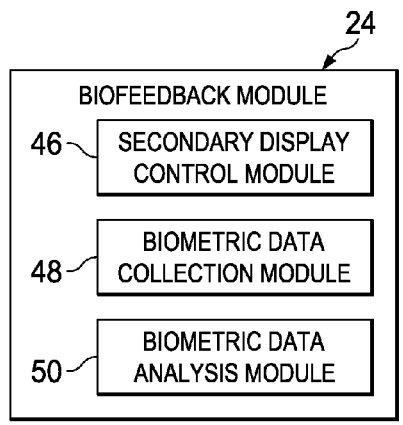
FIG. 6 is a simplified block diagram illustrating an embodiment of an electronic device, in accordance with one embodiment of the present disclosure.

Turning to FIG. 6, FIG. 6 is a simplified block diagram illustrating an embodiment of a portion of electronic device 10, in accordance with one embodiment of the present disclosure. In this particular embodiment, biofeedback module 24 can include a secondary display control module 46, a biometric data collection module 48, and a biometric data analysis module 50. Secondary display control module 46 can be configured to control secondary displays 16*a* and 16*b* and communicate analyzed biometric data to a user. Biometric data collection module 48 can be configured to control first biosensor 42, second biosensor 44, third biosensor 56, and fourth biosensor 58, collect the detected biometric data, and send the collected biometric data to biometric analysis module 50. Biometric analysis module 50 can be configured to analyze the collected biometric data and communicate with secondary display control module 46 to communicate the analysis to the user.

Figure 7:
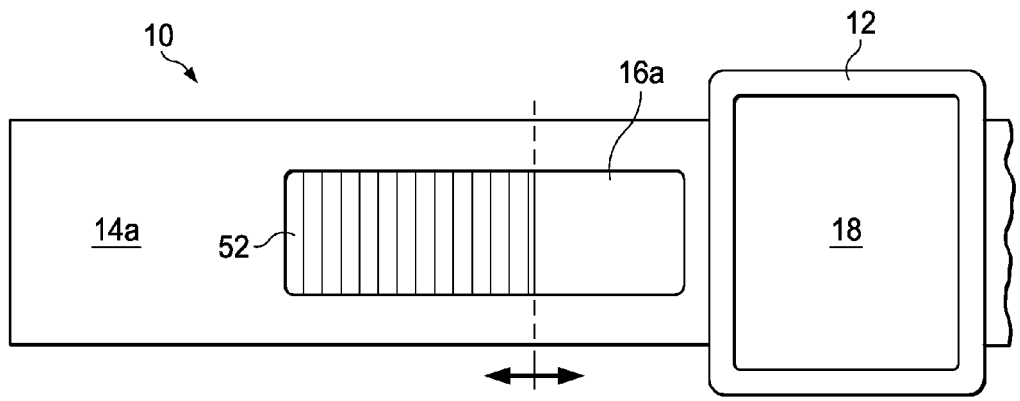
FIG. 7 is a simplified block diagram illustrating an embodiment of an electronic device, in accordance with one embodiment of the present disclosure.

Turning to FIG. 7, FIG. 7 is a simplified block diagram illustrating an embodiment of a portion of electronic device 10, in accordance with one embodiment of the present disclosure. Secondary display 16*a* can include an illuminated region 52. As illustrated in FIG. 7, illuminated region 52 can move based on collected biometric data. For example, if the collected biometric data relates to a heart rate of a user, the area of illuminated region 52 can increase as the heart rate increases or decrease as the heart rate decreases.

Figure 8:
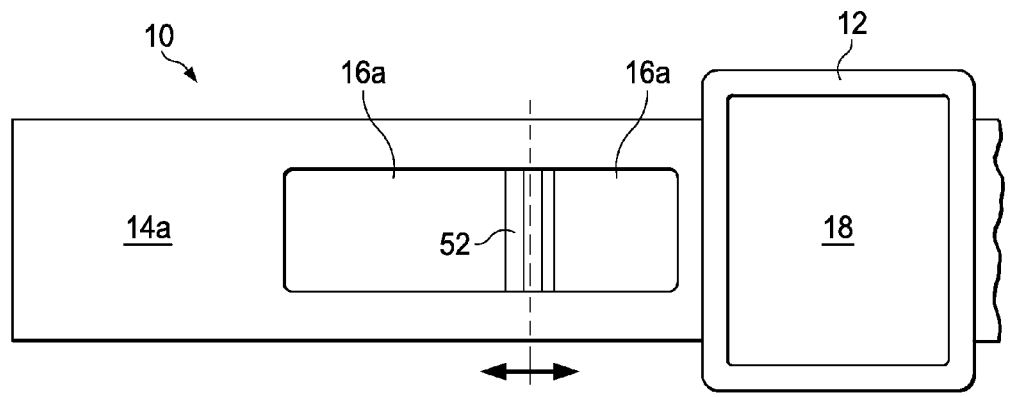
FIG. 8 is a simplified block diagram illustrating an embodiment of an electronic device, in accordance with one embodiment of the present disclosure.

Turning to FIG. 8, FIG. 8 is a simplified block diagram illustrating an embodiment of a portion of electronic device 10, in accordance with one embodiment of the present disclosure. As illustrated in FIG. 8, illuminated region 52 is a bar or line and can move based on collected biometric data. For example, if the collected biometric data relates to a heart rate of a user, the area of illuminated region 52 can move up or forward on secondary display 16*a* as the heart rate increases or move down or backwards on secondary display 16*a* as the heart rate decreases.

Figure 9:
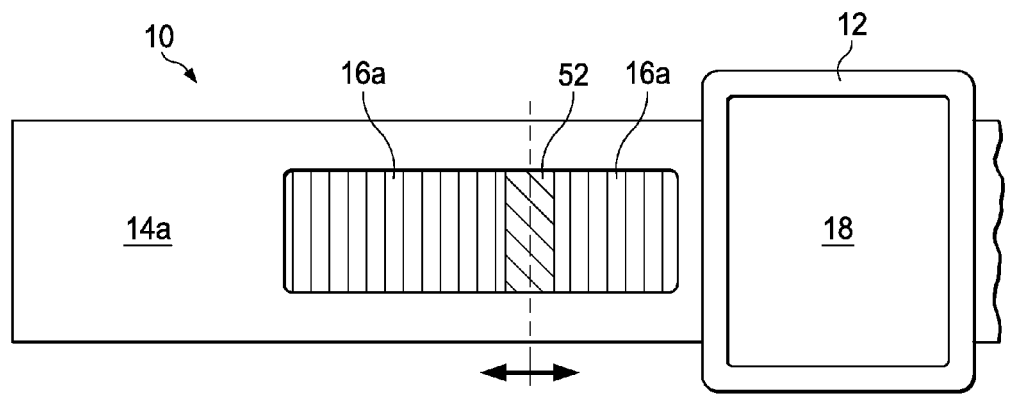
FIG. 9 is a simplified block diagram illustrating an embodiment of an electronic device, in accordance with one embodiment of the present disclosure.

Turning to FIG. 9, FIG. 9 is a simplified block diagram illustrating an embodiment of a portion of electronic device 10, in accordance with one embodiment of the present disclosure. As illustrated in FIG. 9, illuminated region 52 is a bar or line and can move based on collected biometric data. Secondary display 16*a* can display a contrasting background color to enhance the visibility of illuminated region 52.

Figure 10:
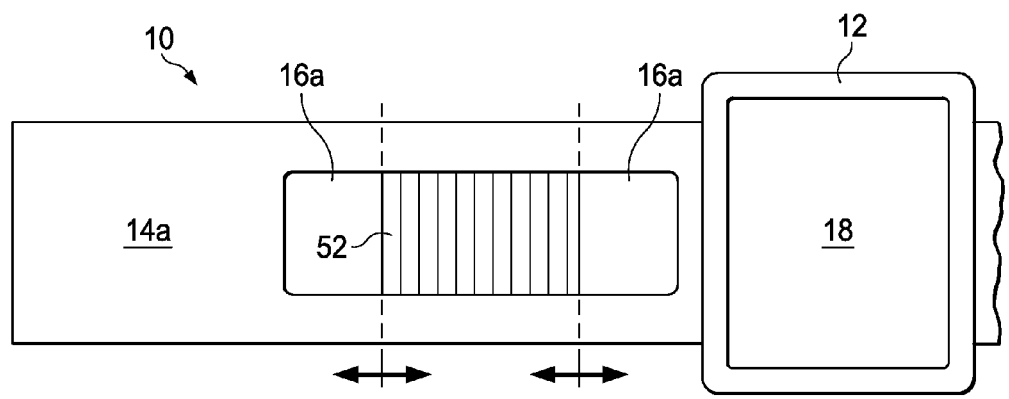
FIG. 10 is a simplified block diagram illustrating an embodiment of an electronic device, in accordance with one embodiment of the present disclosure.

Turning to FIG. 10, FIG. 10 is a simplified block diagram illustrating an embodiment of a portion of electronic device 10, in accordance with one embodiment of the present disclosure. As illustrated in FIG. 10, illuminated region 52 is an area or region. Each side of illuminated region 52 can move independent of the other side or in conjunction with the other side. For example, if illuminated region 52 was communicating the length of time for a workout, illuminated region 52 may start out as a line in the center of secondary display 16a and as the workout progressed, illuminated region 52 may grow to fill in secondary display 16a.

Figure 11:
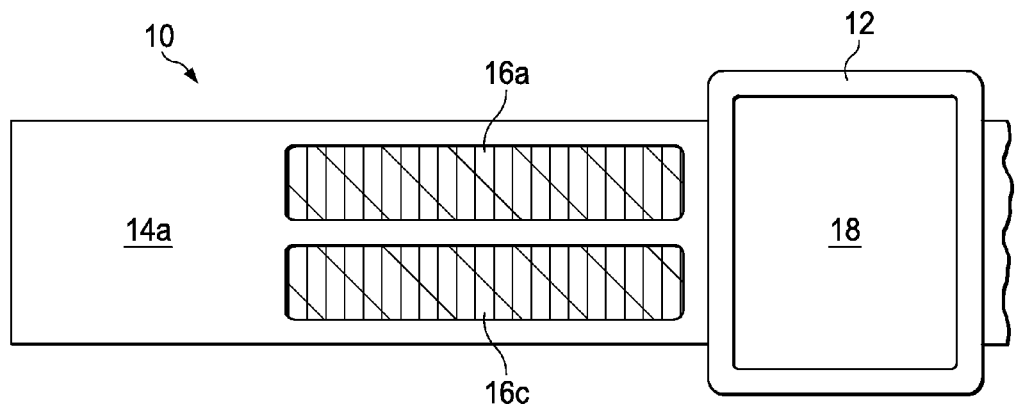
FIG. 11 is a simplified block diagram illustrating an embodiment of an electronic device, in accordance with one embodiment of the present disclosure.

Turning to FIG. 11, FIG. 11 is a simplified block diagram illustrating an embodiment of a portion of electronic device 10, in accordance with one embodiment of the present disclosure. As illustrated in FIG. 11, wrist strap 14a can include secondary display 16a and a secondary display 16c. Secondary display 16a and secondary display 16c may act independent of each other or may have some correlation. For example, secondary display 16a may communicate a heart rate of a user and secondary display 16c may communicate the time remaining in a workout routine. Alternatively, secondary display 16a may communicate a current running pace of a user and secondary display 16c may communicate a desired or target running pace of a user.

Figure 12:
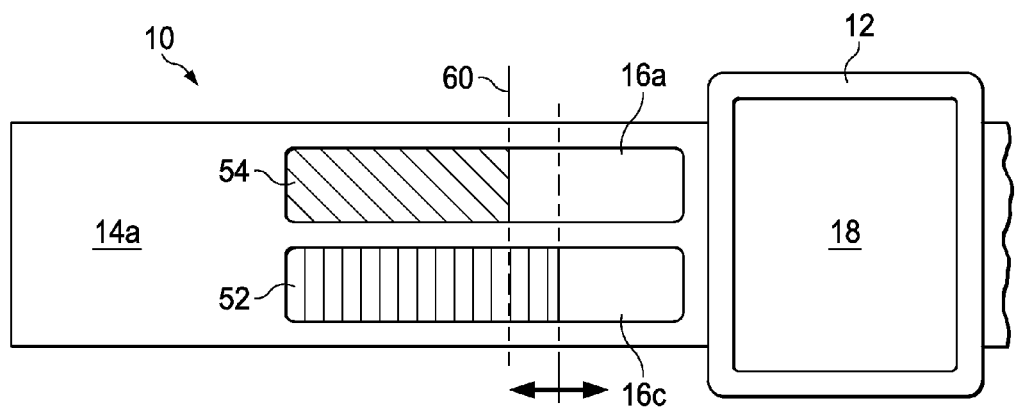
FIG. 12 is a simplified block diagram illustrating an embodiment of an electronic device, in accordance with one embodiment of the present disclosure.

Turning to FIG. 12, FIG. 12 is a simplified block diagram illustrating an embodiment of a portion of electronic device 10, in accordance with one embodiment of the present disclosure. Illuminated region 52 may communicate a current running pace of a user and illuminated target value 54 may communicate a desired or target running pace of a user. As illustrated in FIG. 12, a user would easily be able to determine that they are running at too fast of a pace and would need to slow down. Such information would be important when distance running as runners tend to run too fast during the first parts of the run.

Figure 13:
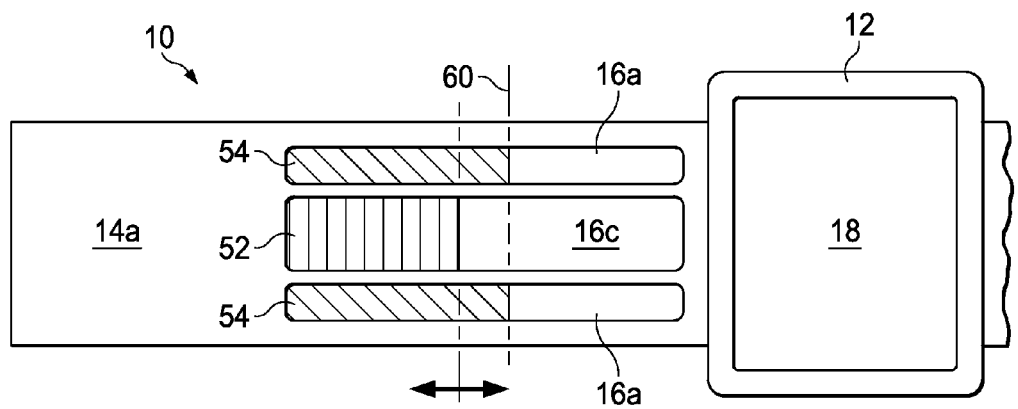
FIG. 13 is a simplified block diagram illustrating an embodiment of an electronic device, in accordance with one embodiment of the present disclosure.

Turning to FIG. 13, FIG. 13 is a simplified block diagram illustrating an embodiment of a portion of electronic device 10, in accordance with one embodiment of the present disclosure. Illuminated region 52 may communicate a current running pace of a user and illuminated target value 54 may communicate a desired or target running pace of a user. As illustrated in FIG. 12, a user would easily be able to determine that they are running at too slow of a pace and would need to speed up.

Figure 14:
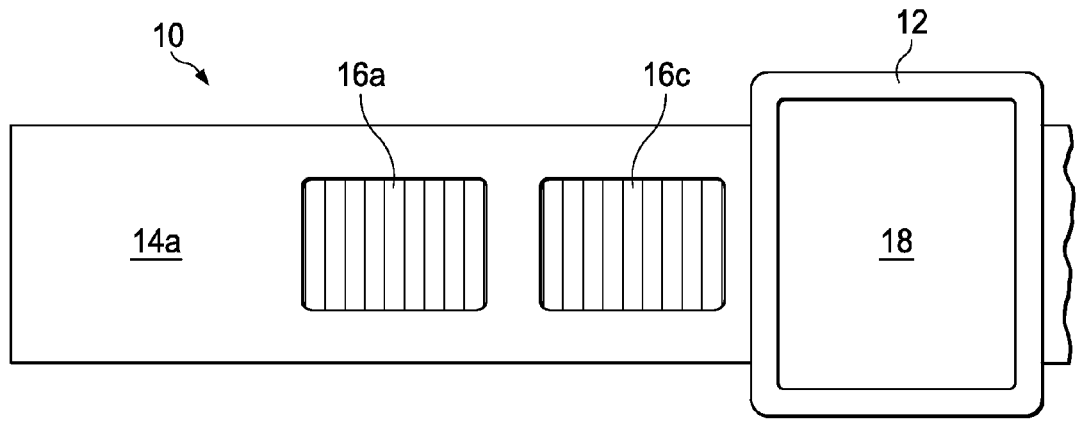
FIG. 14 is a simplified block diagram illustrating an embodiment of an electronic device, in accordance with one embodiment of the present disclosure.
Figure 15:
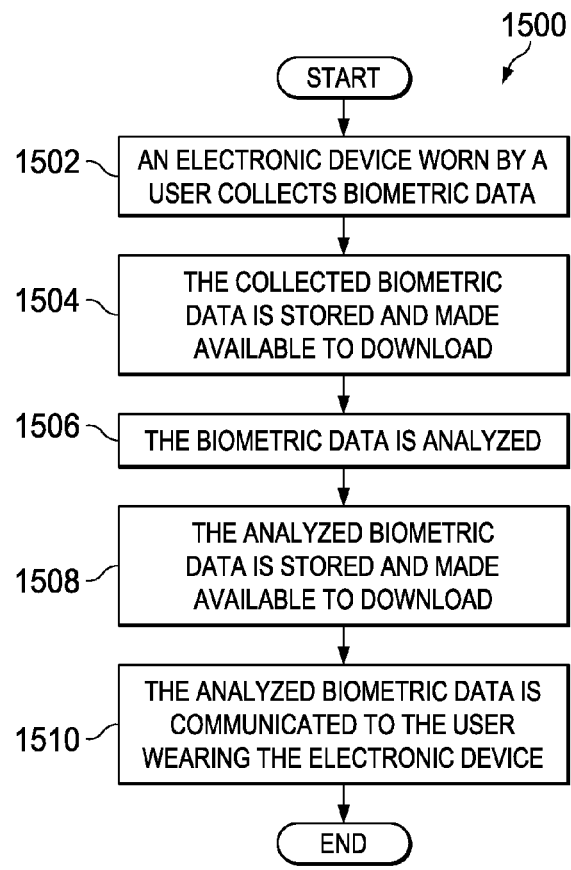
FIG. 15 is a simplified flow diagram illustrating potential operations associated with one embodiment of the present disclosure.

Turning to FIG. 14, FIG. 14 is a simplified block diagram illustrating an embodiment of a portion of electronic device 10, in accordance with one embodiment of the present disclosure. Secondary display 16a and secondary display 16c may act independent of each other or may have some correlation. For example, secondary display 16a may communicate a heart rate of a user and secondary display 16c may communicate the time remaining in a workout routine. The illustrated location of each secondary display and the illustrated profile, shape, or "look" of each illumination region 52 and target region 54 have only been offered for purposes of example and teaching only. Each of these may be varied considerably without departing from the spirit of the present disclosure, or the scope of the appended claims Turning to FIG. 15, FIG. 15 is a simplified flowchart 1500 illustrating example activities of an electronic device to display biometric data. In an embodiment, one or more operations of flow 1500 may be performed by biofeedback module 24. At 1502, an electronic device worn by a user collects biometric data. At 1504, the collected biometric data is stored and made available to download. At 1506, the biometric data is analyzed. At 1508, the analyzed biometric data is stored and made available to download. At 1510, the analyzed biometric data is communicated to the user wearing electronic device.

Figure 16:
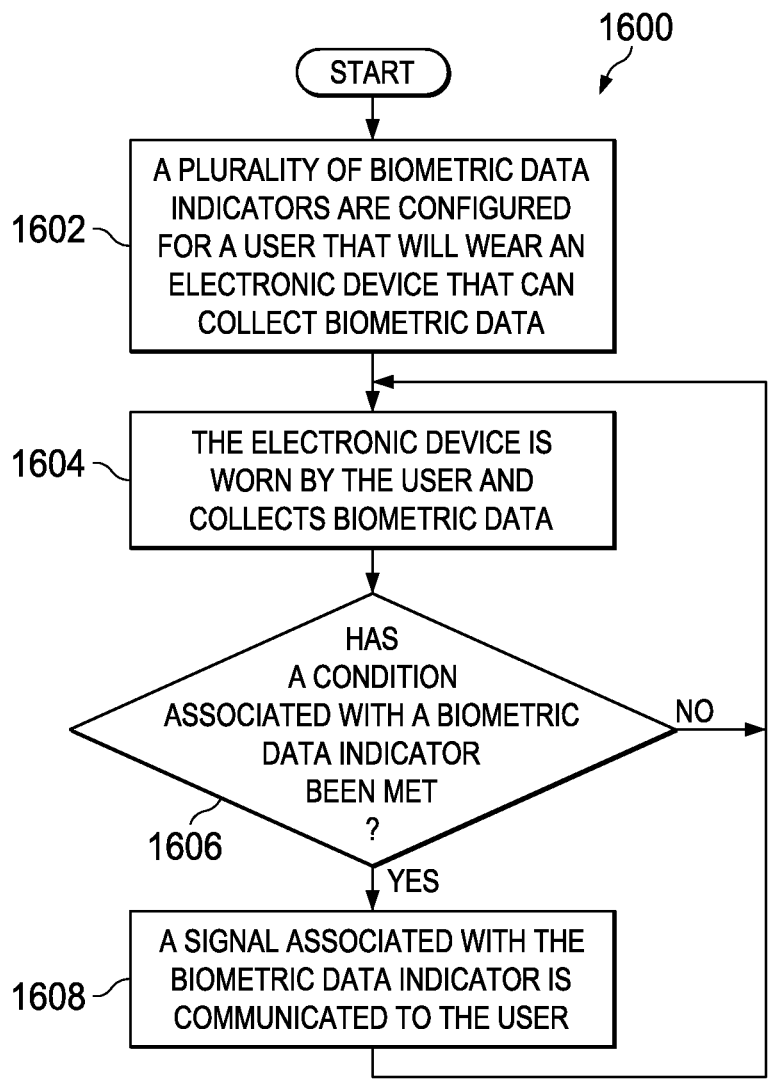
FIG. 16 is a simplified flow diagram illustrating potential operations associated with one embodiment of the present disclosure.

Turning to FIG. 16, FIG. 16 is a simplified flowchart 1600 illustrating example activities of an electronic device to display biometric data. In an embodiment, one or more operations of flow 1600 may be performed by biofeedback module 24. At 1602, a plurality of biometric data indicators are configured for a user that will wear an electronic device that can collect biometric data. At 1604, the electronic device is worn by the user and collects biometric data. At 1606, the system determines if a condition associated with a biometric data indicator has been met. If a condition associated with a biometric indicator has been met, a signal associated with the biometric data indicator is communicated to the user, as in 1608 and the system returns to 1604 and the electronic device continues to collect biometric data. If a condition associated with a biometric indicator has not been met, then the system returns to 1604 and the electronic device continues to collect biometric data.

Figure 17:
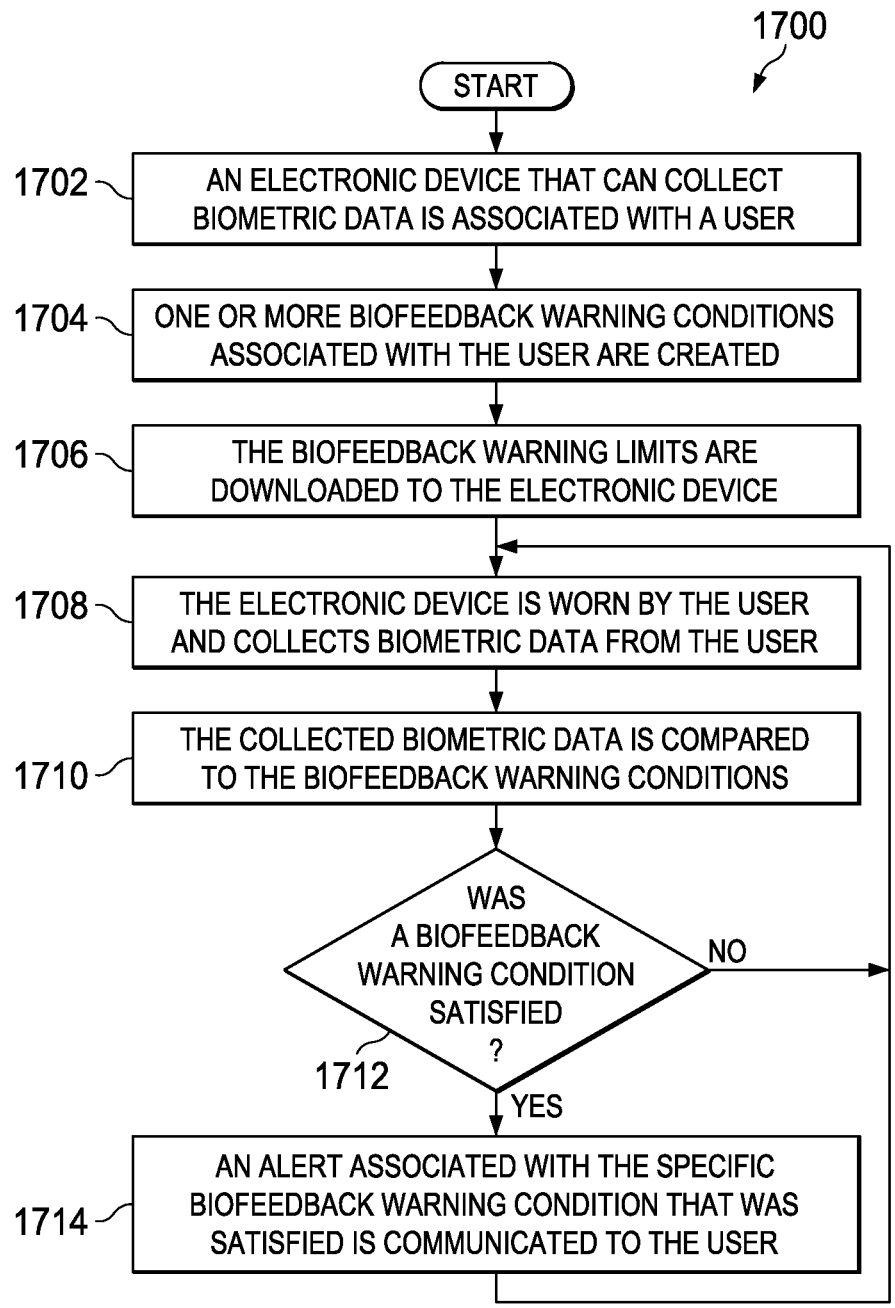
FIG. 17 is a simplified flow diagram illustrating potential operations associated with one embodiment of the present disclosure.

Turning to FIG. 17, FIG. 17 is a simplified flowchart 1700 illustrating example activities of an electronic device to display biometric data. In an embodiment, one or more operations of flow 1700 may be performed by biofeedback module 24. At 1702, an electronic device that can collect biometric data is associated with a user. At 1704, one or more biofeedback warning conditions associated with the user are created. At 1706, the biofeedback warning limits are downloaded to the electronic device. At 1708, the electronic device is worn by the user and collects biometric data from the user. At 1710, the collected biometric data is compared to the biofeedback warning conditions. At 1712, the system determines if a biofeedback warning condition was satisfied. If a biofeedback warning condition was satisfied, an alert associated with the specific biofeedback warning condition that was satisfied is communicated to the user, as in 1714 and the system returns to 1708 and the electronic device continues to collect biometric data. If a biofeedback warning condition was not satisfied, then the system returns to 1708 and electronic device continues to collect biometric data.

Figure 18:
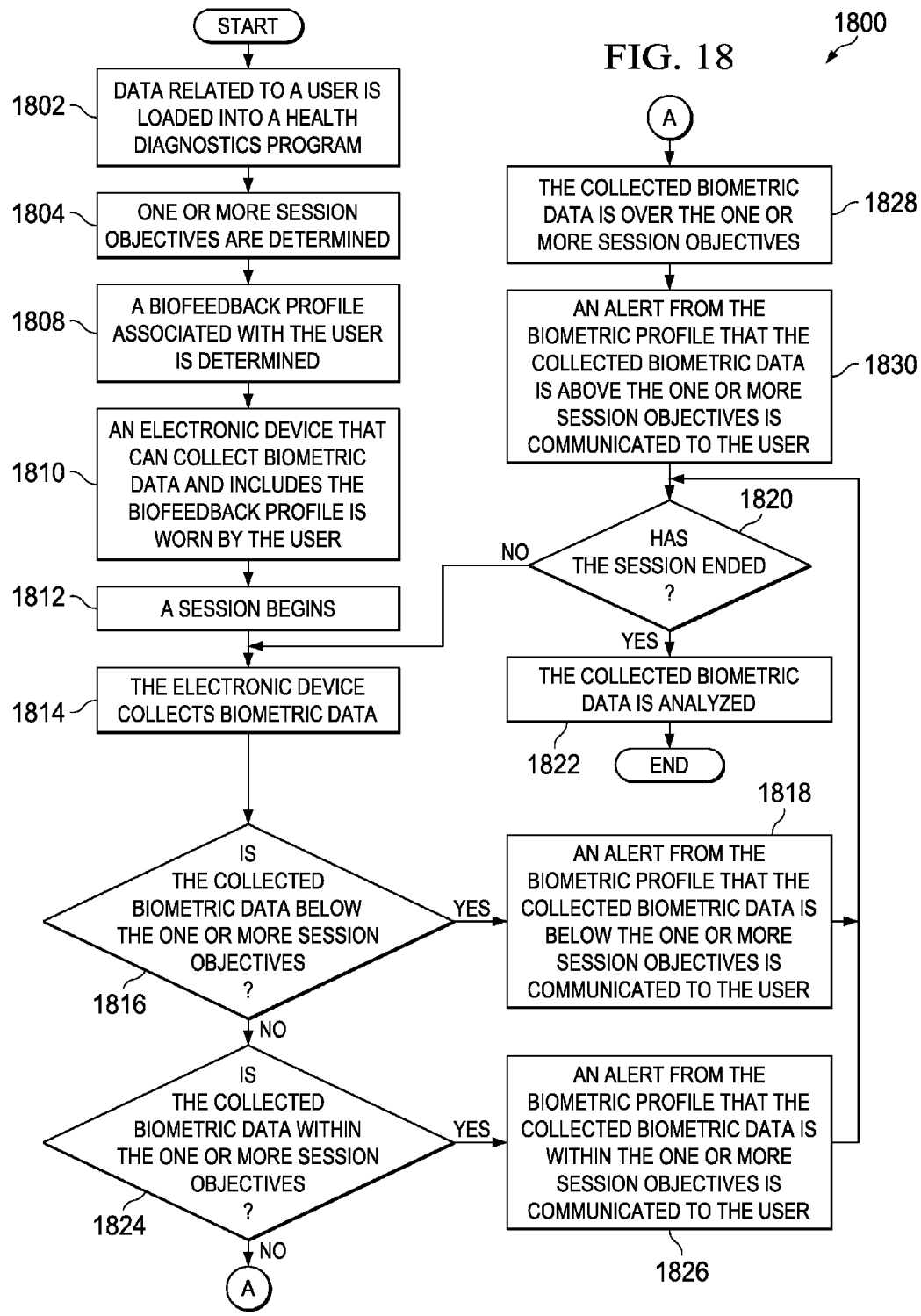
FIG. 18 is a simplified flow diagram illustrating potential operations associated with one embodiment of the present disclosure.

Turning to FIG. 18, FIG. 18 is a simplified flowchart 1800 illustrating example activities of an electronic device to display biometric data. In an embodiment, one or more operations of flow 1800 may be performed by biofeedback module 24. At 1802, data related to a user is loaded into a health diagnostics program. At 1804, one or more session objectives are determined. At 1808, a biofeedback profile associated with the user is determined. At 1810, an electronic device that can collect biometric data and includes the biofeedback profile is worn by the user. At 1812, a session begins. At 1814, the electronic device collects biometric data.

At 1816, the system determines if the collected biometric data is below the one or more session objectives. If the collected biometric data is below the one or more session objectives, then an alert from the biometric profile that the collected biometric data is below the one or more session objectives is communicated to the user, as in 1818. At 1820, the system determines if the session has ended. If the session has not ended, then the electronic device collects biometric data as in 1814. If the session has ended, then the collected biometric data is analyzed as in 1822.

Going back to 1816, if the collected biometric data is not below the one or more session objectives, then the system determines if the collected biometric data is within the one or more session objectives, as in 1824. If the collected biometric data is within the one or more session objectives, then an alert from the biometric profile that the collected biometric data is within the one or more session objectives is communicated to the user, as in 1826 and the system determines if the session has ended, as in 1820. If the system determines that the collected biometric data is not within the one or more session objectives, then the collected biometric data is over the one or more session objectives, as in 1828. At 1830, an alert from the biometric data profile that the collected biometric data is above the one or more session objectives is communicated to the user. At 1820, the system determines if the session has ended.

Figure 19:
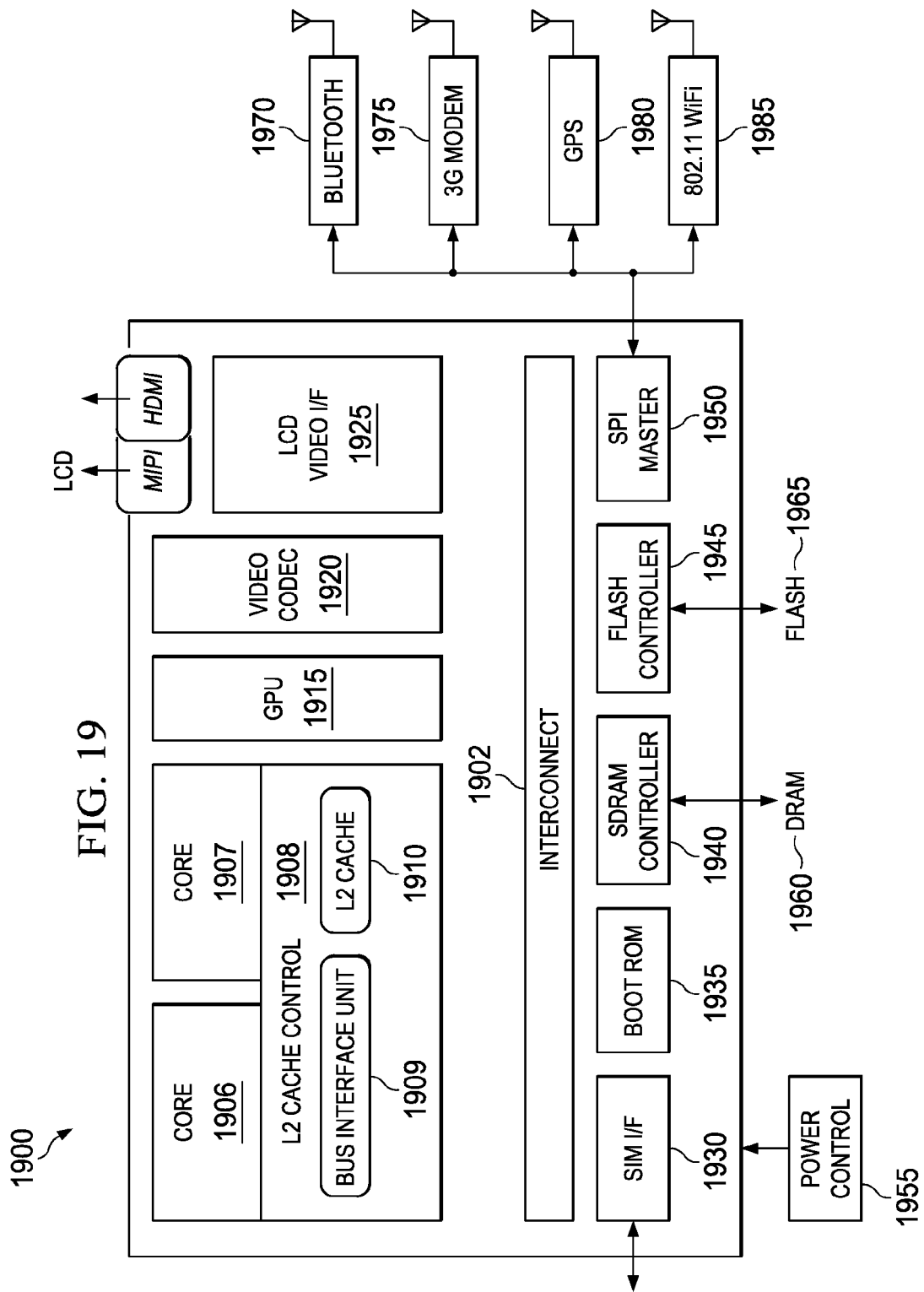
FIG. 19 is a simplified block diagram associated with an example ARM ecosystem system on chip (SOC) of the present disclosure.

FIG. 19 is a simplified block diagram associated with an example ARM ecosystem SOC 1900 of the present disclosure. At least one example implementation of the present disclosure can include the biometric feedback features discussed herein and an ARM component. For example, the example of FIG. 19 can be associated with any ARM core (e.g., A-9, A-15, etc.). Further, the architecture can be part of any type of tablet, smartphone (inclusive of Android™ phones, i-Phones™), i-Pad™, Google Nexus™, Microsoft Surface™, personal computer, server, video processing components, laptop computer (inclusive of any type of notebook), Ultrabook™system, any type of touch-enabled input device, etc.

In this example of FIG. 19, ARM ecosystem SOC 1900 may include multiple cores 1906-1907, an L2 cache control 1908, a bus interface unit 1909, an L2 cache 1910, a graphics processing unit (GPU) 1915, an interconnect 1902, a video codec 1920, and a liquid crystal display (LCD) I/F 1925, which may be associated with mobile industry processor interface (MIPI)/high-definition multimedia interface (HDMI) links that couple to an LDC.

ARM ecosystem SOC 1900 may also include a subscriber identity module (SIM) I/F 1930, a boot read-only memory (ROM) 1935, a synchronous dynamic random access memory (SDRAM) controller 1940, a flash controller 1945, a serial peripheral interface (SPI) master 1950, a suitable power control 1955, a dynamic RAM (DRAM) 1960, and flash 1965. In addition, one or more example embodiment include one or more communication capabilities, interfaces, and features such as instances of Bluetooth™ 1970, a 3G modem 1975, a global positioning system (GPS) 1980, and an 802.11 WiFi 1985.

In operation, the example of FIG. 19 can offer processing capabilities, along with relatively low power consumption to enable computing of various types (e.g., mobile computing, high-end digital home, servers, wireless infrastructure, etc.). In addition, such an architecture can enable any number of software applications (e.g., Android™, Adobe® Flash® Player, Java Platform Standard Edition (Java SE), JavaFX, Linux, Microsoft Windows Embedded, Symbian and Ubuntu, etc.). In at least one example embodiment, the core processor may implement an out-of-order superscalar pipeline with a coupled low-latency level-2 cache.

Figure 20:
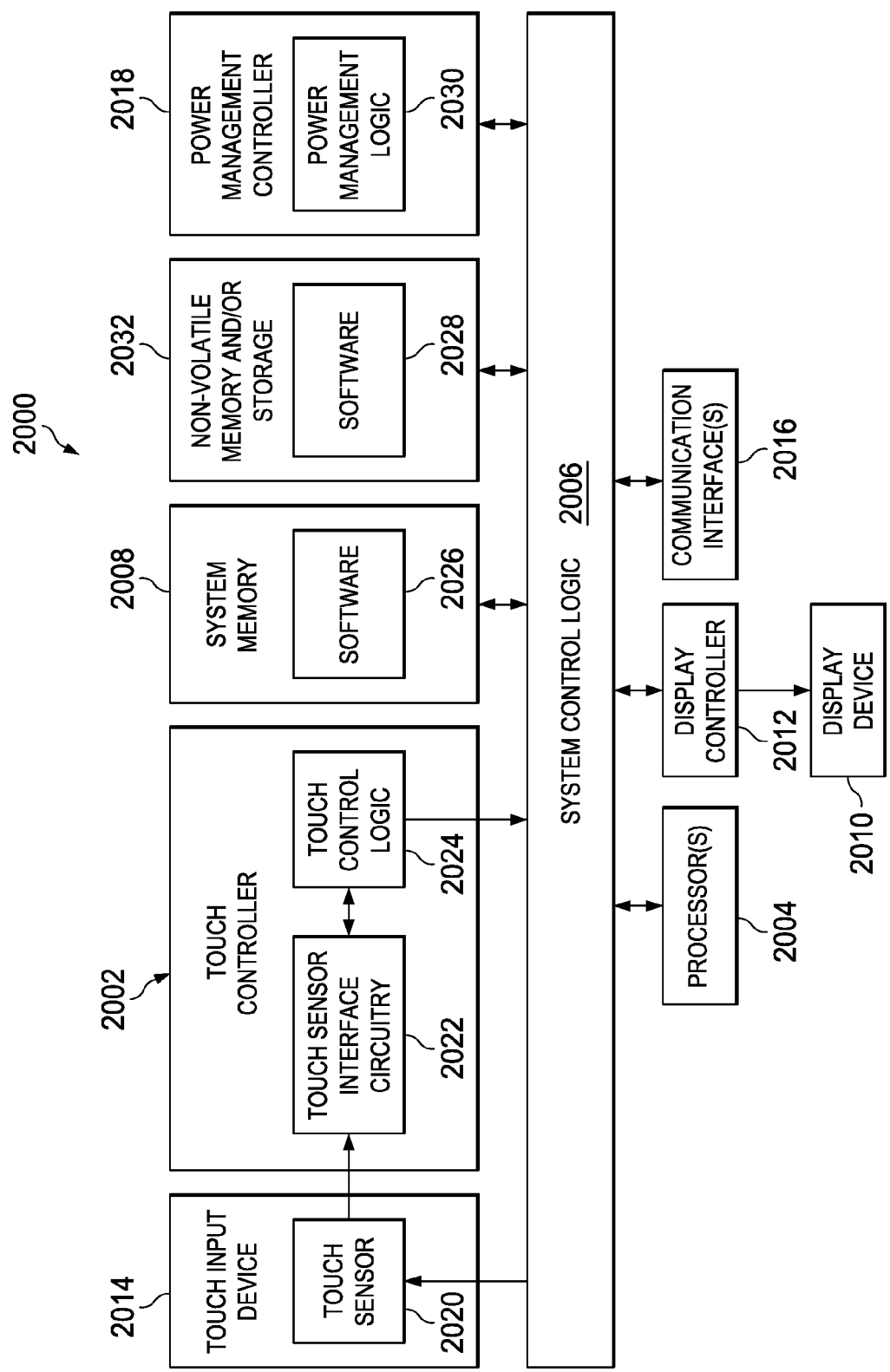
FIG. 20 is a simplified block diagram illustrating example logic that may be used to execute activities associated with the present disclosure.

FIG. 20 is a simplified block diagram illustrating potential electronics and logic that may be associated with any of the biometric feedback operations discussed herein. In at least one example embodiment, system 2000 can include a touch controller 2002, one or more processors 2004, system control logic 2006 coupled to at least one of processor(s) 2004, system memory 2008 coupled to system control logic 2006, non-volatile memory and/or storage device(s) 2032 coupled to system control logic 2006, display controller 2012 coupled to system control logic 2032, display controller 2012 coupled to a display device 2010, touch input device 2014 coupled to system control logic 2006, power management controller 2018 coupled to system control logic 2006, and/or communication interfaces 2016 coupled to system control logic 2006. Touch input device 2014 can include touch sensor 2020.

System control logic 2006, in at least one embodiment, can include any suitable interface controllers to provide for any suitable interface to at least one processor 2004 and/or to any suitable device or component in communication with system control logic 2006. System control logic 2006, in at least one example embodiment, can include one or more memory controllers to provide an interface to system memory 2008. System memory 2008 may be used to load and store data and/or instructions, for example, for system 2000. System memory 2008, in at least one example embodiment, can include any suitable volatile memory, such as suitable dynamic random access memory (DRAM) for example. System control logic 2006, in at least one example embodiment, can include one or more I/O controllers to provide an interface to display device 2010, touch controller 2002, and non-volatile memory and/or storage device(s) 2032.

Non-volatile memory and/or storage device(s) 2032 may be used to store data and/or instructions, for example within software 2028. Non-volatile memory and/or storage device(s) 2032 may include any suitable non-volatile memory, such as flash memory for example, and/or may include any suitable non-volatile storage device(s), such as one or more hard disc drives (HDDs), one or more compact disc (CD) drives, and/or one or more digital versatile disc (DVD) drives for example.

Power management controller 2018 may include power management logic 2030 configured to control various power management and/or power saving functions disclosed herein or any part thereof. In at least one example embodiment, power management controller 2018 is configured to reduce the power consumption of components or devices of system 2000 that may either be operated at reduced power or turned off when the electronic device is in a closed configuration. For example, in at least one example embodiment, when the electronic device is in a closed configuration, power management controller 2018 performs one or more of the following: power down the unused portion of the display and/or any backlight associated therewith; allow one or more of processor(s) 2004 to go to a lower power state if less computing power is required in the closed configuration; and shutdown any devices and/or components that are unused when an electronic device is in the closed configuration.

Communications interface(s) 2016 may provide an interface for system 2000 to communicate over one or more networks and/or with any other suitable device. Communications interface(s) 2016 may include any suitable hardware and/or firmware. Communications interface(s) 2016, in at least one example embodiment, may include, for example, a network adapter, a wireless network adapter, a telephone modem, and/or a wireless modem.

System control logic 2006, in at least one example embodiment, can include one or more I/O controllers to provide an interface to any suitable input/output device(s) such as, for example, an audio device to help convert sound into corresponding digital signals and/or to help convert digital signals into corresponding sound, a camera, a camcorder, a printer, and/or a scanner.

For at least one example embodiment, at least one processor 2004 may be packaged together with logic for one or more controllers of system control logic 2006. In at least one example embodiment, at least one processor 2004 may be packaged together with logic for one or more controllers of system control logic 2006 to form a System in Package (SiP). In at least one example embodiment, at least one processor 2004 may be integrated on the same die with logic for one or more controllers of system control logic 2006. For at least one example embodiment, at least one processor 2004 may be integrated on the same die with logic for one or more controllers of system control logic 2006 to form a System on Chip (SoC).

For touch control, touch controller 2002 may include touch sensor interface circuitry 2022 and touch control logic 2024. Touch sensor interface circuitry 2022 may be coupled to detect touch input over a first touch surface layer and a second touch surface layer of a display (i.e., display device 2010). Touch sensor interface circuitry 2022 may include any suitable circuitry that may depend, for example, at least in part on the touch-sensitive technology used for a touch input device. Touch sensor interface circuitry 2022, in one embodiment, may support any suitable multi-touch technology. Touch sensor interface circuitry 2022, in at least one embodiment, can include any suitable circuitry to convert analog signals corresponding to a first touch surface layer and a second surface layer into any suitable digital touch input data. Suitable digital touch input data for at least one embodiment may include, for example, touch location or coordinate data.

Touch control logic 2024 may be coupled to help control touch sensor interface circuitry 2022 in any suitable manner to detect touch input over a first touch surface layer and a second touch surface layer. Touch control logic 2024 for at least one example embodiment may also be coupled to output in any suitable manner digital touch input data corresponding to touch input detected by touch sensor interface circuitry 2022. Touch control logic 2024 may be implemented using any suitable logic, including any suitable hardware, firmware, and/or software logic (e.g., non-transitory tangible media), that may depend, for example, at least in part on the circuitry used for touch sensor interface circuitry 2022. Touch control logic 2024 for at least one embodiment may support any suitable multi-touch technology.

Touch control logic 2024 may be coupled to output digital touch input data to system control logic 2006 and/or at least one processor 2004 for processing. At least one processor 2004 for at least one embodiment may execute any suitable software to process digital touch input data output from touch control logic 2024. Suitable software may include, for example, any suitable driver software and/or any suitable application software. As illustrated in FIG. 20, system memory 2008 may store suitable software 2026 and/or non-volatile memory and/or storage device(s).

Note that in some example implementations, the functions outlined herein may be implemented in conjunction with logic that is encoded in one or more tangible, non-transitory media (e.g., embedded logic provided in an application-specific integrated circuit (ASIC), in digital signal processor (DSP) instructions, software [potentially inclusive of object code and source code] to be executed by a processor, or other similar machine, etc.). In some of these instances, memory elements can store data used for the operations described herein. This can include the memory elements being able to store software, logic, code, or processor instructions that are executed to carry out the activities described herein. A processor can execute any type of instructions associated with the data to achieve the operations detailed herein. In one example, the processors could transform an element or an article (e.g., data) from one state or thing to another state or thing. In another example, the activities outlined herein may be implemented with fixed logic or programmable logic (e.g., software/computer instructions executed by a processor) and the elements identified herein could be some type of a programmable processor, programmable digital logic (e.g., a field programmable gate array (FPGA), a DSP, an erasable programmable read only memory (EPROM), electrically erasable programmable read-only memory (EEPROM)) or an ASIC that can include digital logic, software, code, electronic instructions, or any suitable combination thereof.

It is imperative to note that all of the specifications, dimensions, and relationships outlined herein (e.g., location, position, number or elements, color, height, width, length, materials, etc.) have only been offered for purposes of example and teaching only. Each of these data may be varied considerably without departing from the spirit of the present disclosure, or the scope of the appended claims. The specifications apply only to one non-limiting example and, accordingly, they should be construed as such. In the foregoing description, example embodiments have been described. Various modifications and changes may be made to such embodiments without departing from the scope of the appended claims. The description and drawings are, accordingly, to be regarded in an illustrative rather than a restrictive sense.

Numerous other changes, substitutions, variations, alterations, and modifications may be ascertained to one skilled in the art and it is intended that the present disclosure encompass all such changes, substitutions, variations, alterations, and modifications as falling within the scope of the appended claims. In order to assist the United States Patent and Trademark Office (USPTO) and, additionally, any readers of any patent issued on this application in interpreting the claims appended hereto, Applicant wishes to note that the Applicant: (a) does not intend any of the appended claims to invoke paragraph six (6) of 35 U.S.C. section 112 as it exists on the date of the filing hereof unless the words "means for" or "step for" are specifically used in the particular claims; and (b) does not intend, by any statement in the specification, to limit this disclosure in any way that is not otherwise reflected in the appended claims.

OTHER NOTES AND EXAMPLES

Example A1 is an electronic device that includes a main housing, where the main housing includes a display, a wrist strap that allows the main housing to be secured to a user, and a secondary display located on the wrist strap. The secondary display can communicate information to the user.

In Example A2, the subject matter of Example A1 may optionally include at least one biosensor to collect biometric data from the user.

In Example A3, the subject matter of any of the preceding 'A' Examples can optionally include where the collected biometric data is analyzed and the analyzed biometric data is communicated to the user.

In Example A4, the subject matter of any of the preceding 'A' Examples can optionally include where the analyzed biometric data is stored and made available for downloading.

In Example A5, the subject matter of any of the preceding 'A' Examples can optionally include a plurality of secondary displays located on the wrist strap.

In Example A6, the subject matter of any of the preceding 'A' Examples can optionally include where each of the plurality of secondary displays communicates different information to the user.

In Example A7, the subject matter of any of the preceding 'A' Examples can optionally include where one of the plurality of secondary displays communicates a target to a user and a different secondary display communicates analyzed biometric data related to the target to the user.

In Example A8, the subject matter of any of the preceding 'A' Examples can optionally include where the secondary display communicates a first alarm when a first threshold is satisfied and a second alarm when a second threshold is satisfied, where the first alarm is different than the second alarm.

In Example A9, the subject matter of any of the preceding 'A' Examples can optionally include where the at least one segment includes a center tooth to mate with a toothed disc of the electronic device to resist rotation between the first housing and the second housing.

Example AA1 is an electronic device that includes a main housing, a main display in the main housing, a wrist strap that allows the main housing to be secured to a user such that the main display is located on top of a wrist of the user, and a secondary display located on the wrist strap, where the secondary display communicates information to the user without the user having to turn the wrist.

In Example AA2, the subject matter of Example A1 may optionally include at least one biosensor to collect biometric data from the user.

In Example AA3, the subject matter of any of the preceding 'A' Examples can optionally include where the collected biometric data is analyzed and the analyzed biometric data is communicated to the user.

In Example AA4, the subject matter of any of the preceding 'A' Examples can optionally include where the analyzed biometric data is stored and made available for downloading.

In Example AA5, the subject matter of any of the preceding 'A' Examples can optionally include a plurality of secondary displays located on the wrist strap.

In Example AA6, the subject matter of any of the preceding 'A' Examples can optionally include where each of the plurality of secondary displays communicates different information to the user.

In Example AA7, the subject matter of any of the preceding 'A' Examples can optionally include where one of the plurality of secondary displays communicates a target to a user and a different secondary display communicates analyzed biometric data related to the target to the user.

In Example AA8, the subject matter of any of the preceding 'A' Examples can optionally include the secondary display communicates a first alarm when a first threshold is satisfied and a second alarm when a second threshold is satisfied, where the first alarm is different than the second alarm Example M1 is a method that includes receiving biometric data from a user, at an electronic device worn by the user, wherein the electronic device includes a main housing and the main housing includes a display, analyzing the biometric data, and communicating the analyzed biometric data to the user on a secondary display located on a wrist strap of the electronic device.

In Example M2, the subject matter of any of the preceding 'M' Examples can optionally include where the biometric data is received from a biosensor located on the electronic device.

In Example M3, the subject matter of any of the preceding 'M' Examples can optionally include communicating a first alarm when the analyzed biometric data satisfies a first threshold, and communicating a second alarm when the analyzed biometric data satisfies a second threshold, where the first alarm is different than the second alarm.

In Example M4, the subject matter of any of the preceding 'M' Examples can optionally include where the biometric data is received by a first biosensor located on the electronic device.

In Example, M5, the subject matter of any of the preceding 'M' Examples can optionally include receiving a second type of biometric data from a second biosensor located on the electronic device, analyzing the second type of biometric data, and communicating the second type of analyzed biometric data to the user on a second secondary display located on the wrist strap.

In Example M6, the subject matter of any of the preceding 'M' Examples can optionally include where analyzing the biometric data includes comparing the received biometric data to a threshold.

In Example M7, the subject matter of any of the preceding 'M' Examples can optionally include where the threshold is related to a medical condition of the user.

In Example M8, the subject matter of any of the preceding 'M' Examples can optionally include where the threshold is a number of heart beats per minute of the user.

An example system S1 can include means for receiving biometric data from a user, means for analyzing the biometric data, and means for communicating the analyzed biometric data to the user on a secondary display located on a wrist strap of an electronic device worn by the user. In an example, the user does not need to turn their wrist to view the communicated analyzed biometric data.

An example system S2 can include means for communicating a first alarm when the analyzed biometric data satisfies a first threshold and means for communicating a second alarm when the analyzed biometric data satisfies a second threshold, wherein the first alarm is different than the second alarm.

Example X1 is a machine-readable storage medium including machine-readable instructions to implement a method or realize an apparatus as in any one of the Examples A1-A9, AA1-AA8, and M1-M8. Example Y1 is an apparatus comprising means for performing of any of the Example methods M1-M8. In Example Y2, the subject matter of Example Y1 can optionally include the means for performing the method comprising a processor and a memory. In Example Y3, the subject matter of Example Y2 can optionally include the memory comprising machine-readable instructions.

What is claimed is:

1. An electronic device, comprising:
   a main housing, wherein the main housing includes a display;
   a wrist strap that allows the main housing to be secured to a user;
   a first biosensor to collect first biodata;
   a second biosensor to collect second biodata, wherein the first biodata is different than the second biodata;
   a first secondary display located on the wrist strap, wherein the first secondary display communicates biometric information related to the collected first biodata to the user;
   a second secondary display located on the wrist strap, wherein the second secondary display communicates biometric information related to the collected second biodata to the user, wherein the first secondary display and the second secondary display communicate different information to the user; and a third secondary display, wherein the third secondary display communicates pace data to the user.

2. The electronic device of claim 1, further comprising: a third biosensor to collect third biometric data from the user, wherein the third biometric data is displayed on the third secondary display along with the pace data.

3. The electronic device of claim 2, wherein the collected first biometric data is analyzed and the analyzed first biometric data is communicated to the user.

4. The electronic device of claim 3, wherein the analyzed first biometric data is stored and made available for downloading.

5. The electronic device of claim 1, further comprising: a plurality of secondary displays located on one side of the wrist strap.

6. The electronic device of claim 5, wherein one of the plurality of secondary displays communicates a target to a user and a different secondary display communicates analyzed first biometric data related to the target to the user.

7. The electronic device of claim 1, wherein the first secondary display communicates a first alarm when a first threshold is satisfied and a second alarm when a second threshold is satisfied, wherein the first alarm is different than the second alarm.

8. A method, comprising:
receiving first biometric data and second biometric data from a user, at an electronic device worn by the user, wherein the first biometric data is different than the second biometric data, wherein the electronic device includes a main housing and the main housing includes a display;
analyzing the first biometric data;
communicating the analyzed first biometric data to the user on a first secondary display located on a wrist strap of the electronic device;
analyzing the second biometric data;
communicating the analyzed second biometric data to the user on a second secondary display located on the wrist strap of the electronic device, wherein the first secondary display and the second secondary display communicate different information to the user; and
communicating pace data to the user on a third secondary display.

9. The method of claim 8, wherein the first biometric data is received from a first biosensor located on the electronic device.

10. The method of claim 8, further comprising:
communicating a first alarm when the analyzed first biometric data satisfies a first threshold; and
communicating a second alarm when the analyzed first biometric data satisfies a second threshold, wherein the first alarm is different than the second alarm.

11. The method of claim 8, further comprising:
receiving a third type of biometric data from a third biosensor located on the electronic device;
analyzing the third type of biometric data; and
communicating the third type of analyzed biometric data to the user on the third secondary display located on the wrist strap.

12. The method of claim 8, wherein analyzing the first biometric data includes comparing the received first biometric data to a threshold.

13. The method of claim 12, wherein the threshold is related to a medical condition of the user.

14. The method of claim 13, wherein the threshold is a number of heart beats per minute of the user.

15. An electronic device, comprising:
a main housing;
a main display in the main housing;
a wrist strap that allows the main housing to be secured to a user such that the main display is located on top of a wrist of the user;
a first biosensor to collect first biodata from the user;
a second biosensor to collect second biodata from the user;
a first secondary display located on the wrist strap, wherein the first secondary display communicates biometric information related to the collected first biodata to the user without the user having to turn the wrist;
a second secondary display located on the wrist strap, wherein the second secondary display communicates biometric information related to the collected second biodata to the user without the user having to turn the wrist, wherein the first secondary display and the second secondary display communicate different information to the user; and
a third secondary display, wherein the third secondary display communicates pace data to the user.

16. The electronic device of claim 15, further comprising: a third biosensor to collect third biodata from the user.

17. The electronic device of claim 15, wherein the collected first biodata is analyzed and the analyzed first biodata is communicated to the user.

18. The electronic device of claim 15, wherein the analyzed first biodata is stored and made available for downloading.

19. The electronic device of claim 15, further comprising: a plurality of secondary displays located on one side of the wrist strap.

20. The electronic device of claim 19, wherein each of the plurality of secondary displays communicates different information to the user.

21. The electronic device of claim 19, wherein one of the plurality of secondary displays communicates a target to a user and a different secondary display communicates analyzed first biodata related to the target to the user.

22. The electronic device of claim 15, wherein the first secondary display communicates a first alarm when a first threshold is satisfied and a second alarm when a second threshold is satisfied, wherein the first alarm is different than the second alarm.

23. A system, comprising:
means for receiving first biometric data and second biometric data from a user;
means for analyzing the first biometric data;
means for communicating the analyzed first biometric data to the user on a first secondary display located on a wrist strap of an electronic device worn by the user, wherein the user does not need to turn their wrist to view the communicated analyzed biometric data;
means for analyzing the second biometric data;
means for communicating the analyzed second biometric data to the user on a second secondary display located on the wrist strap of the electronic device, wherein the first secondary display and the second secondary display communicate different information to the user; and
means for communicating pace data to the user on a third secondary display.

24. The system of claim 23, further comprising:
means for communicating a first alarm when the analyzed first biometric data satisfies a first threshold; and means for communicating a second alarm when the analyzed first biometric data satisfies a second threshold, wherein the first alarm is different than the second alarm.

25. The electronic device of claim 1, further comprising: memory, wherein the memory includes session data and the pace data communicated to the user is related to the session data.

\* \* \* \* \*